US007601361B2

(12) United States Patent
Lu et al.

(10) Patent No.: US 7,601,361 B2
(45) Date of Patent: Oct. 13, 2009

(54) PROCESS FOR PROVIDING ANTIMICROBIAL SURFACES

(75) Inventors: Helen S. M. Lu, Wallingford, PA (US); John S. Chapman, New London Township, PA (US); Albert Gordon Anderson, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 334 days.

(21) Appl. No.: 11/242,395

(22) Filed: Oct. 3, 2005

(65) Prior Publication Data

US 2007/0077348 A1 Apr. 5, 2007

(51) Int. Cl.
*A61K 9/00* (2006.01)
*A61F 13/00* (2006.01)
*A61K 38/16* (2006.01)
*A61K 38/10* (2006.01)

(52) U.S. Cl. .................. 424/400; 514/12; 514/13; 514/14; 424/402; 424/422; 424/429

(58) Field of Classification Search ................. None
See application file for complete search history.

(56) References Cited

U.S. PATENT DOCUMENTS

| | | | |
|---|---|---|---|
| 4,182,695 A | | 1/1980 | Horn et al. |
| 5,589,563 A | | 12/1996 | Ward et al. |
| 5,847,047 A | * | 12/1998 | Haynie ............ 525/54.1 |
| 6,740,719 B1 | * | 5/2004 | Weinert ............ 526/295 |
| 6,927,254 B2 | | 8/2005 | Melchiors et al. |
| 2003/0109452 A1 | | 6/2003 | Owen |
| 2004/0120982 A1 | * | 6/2004 | Diana et al. ........ 424/429 |
| 2004/0121939 A1 | * | 6/2004 | Diana ............ 514/2 |

FOREIGN PATENT DOCUMENTS

| | | |
|---|---|---|
| EP | 1 174 027 A1 | 1/2002 |
| WO | WO 92/01462 A1 | 2/1992 |
| WO | WO 02/064183 A1 | 8/2002 |
| WO | WO 2004/056402 A2 | 7/2004 |
| WO | WO 2004/056407 A2 | 7/2004 |
| WO | WO 2005/019241 A2 | 3/2005 |

OTHER PUBLICATIONS

S.E. Blondelle and R.A. Houghten. Biochemistry (1992) 31(50), pp. 12688-12694.*
D. Eisenberg et al., Analysis of Membrane and Surface Protein Sequences With the Hydrophobic Moment Plot, J. Mol. Biol., vol. 179:125-142, 1984.
Michael Zasloff, Antimicrobial Peptides of Multicellular Organisms, Nature, vol. 415:389-395, 2002.
Richard M. Epand et al., Diversity of Antimicrobial Peptides and Their Mechanisms of Action, Biochimica Et Biophysica Acta, vol. 1462:11-28, 1999.
Yechiel Shai, Mechanism of the Binding, Insertion and Destabilization of Phospholipid Bilayer Membranes by Alpha-Helical Antimicrobial and Cell Non-Selective Membrane-Lytic Peptides, Biochimica Et Biophysica Acta, vol. 1462:55-70, 1999.
Katsumi Matsuzaki et al., Why and How Are Peptide-Lipid Interactions Utilized for Self-Defense? Magainins and Tachyplesins as Archetypes, Biochimica Et Biophysica Acta, vol. 1462:1-10, 1999.
Jian Lin et al., Antimicrobial Treatment of Nylon, Journal of Applied Polymer Science, vol. 81:943-947, 2001.
Lin Yang et al., Crystallization of Antimicrobial Pores in Membranes: Magainin and Protegrin, Biophysical Journal, vol. 79:2002-2009, 2000.
William F. Degrado et al., Design, Synthesis and Characterization of a Cytotoxic Peptide With Melittin-Like Activity, J. American Chemical Soc., vol. 103:679-681, 1981.
N. A. Orlova et al., Halosilanes in the Synthesis of N-(Halomethyl) Derivatives of Lactams, N-Methylcarboxamides, and Imides, Russian Journal of General Chemistry, EN:61, 9.2; 1991; 1875-1881.
Harold E. Zaugg et al., Alpha-Amidoalkylations at Carbon, Org. React., Chapter 2, vol. 14:52-269, 1965.

* cited by examiner

*Primary Examiner*—Andrew D Kosar

(57) ABSTRACT

Processes for providing durable antimicrobial surfaces are disclosed that comprise treating a polymer substrate surface with formaldehyde followed by treatment with an antimicrobial peptide. Further embodiments include articles, including medical devices, characterized by a durable antimicrobial surface provided by the processes of the invention.

25 Claims, No Drawings

SEQUENCE LISTING

<160> NUMBER OF SEQ ID NOS: 29

<210> SEQ ID NO 1
<211> LENGTH: 17
<212> TYPE: PRT
<213> ORGANISM: Artificial
<220> FEATURE:
<223> OTHER INFORMATION: Description of artificial sequence:
      Antimicrobial peptide

<400> SEQUENCE: 1

Pro Lys Gly Leu Lys Lys Leu Leu Lys Gly Leu Lys Lys Leu Leu Lys
1               5                   10                  15

Leu

<210> SEQ ID NO 2
<211> LENGTH: 16
<212> TYPE: PRT
<213> ORGANISM: Artificial
<220> FEATURE:
<223> OTHER INFORMATION: Description of artificial sequence:
      Antimicrobial peptide

<400> SEQUENCE: 2

Lys Gly Leu Lys Lys Leu Leu Lys Gly Leu Lys Lys Leu Leu Lys Leu
1               5                   10                  15

<210> SEQ ID NO 3
<211> LENGTH: 16
<212> TYPE: PRT
<213> ORGANISM: Artificial
<220> FEATURE:
<223> OTHER INFORMATION: Description of artificial sequence:
      Antimicrobial peptide

<400> SEQUENCE: 3

Lys Gly Leu Lys Lys Leu Leu Lys Leu Leu Lys Lys Leu Leu Lys Leu
1               5                   10                  15

<210> SEQ ID NO 4
<211> LENGTH: 14
<212> TYPE: PRT
<213> ORGANISM: Artificial
<220> FEATURE:
<223> OTHER INFORMATION: Description of artificial sequence:
      Antimicrobial peptide

<400> SEQUENCE: 4

Leu Lys Lys Leu Leu Lys Leu Leu Lys Lys Leu Leu Lys Leu
1               5                   10

<210> SEQ ID NO 5
<211> LENGTH: 12
<212> TYPE: PRT
<213> ORGANISM: Artificial
<220> FEATURE:
<223> OTHER INFORMATION: Description of artificial sequence:
      Antimicrobial peptide

<400> SEQUENCE: 5

Leu Lys Lys Leu Leu Lys Leu Leu Lys Lys Leu Leu
1               5                   10

```
<210> SEQ ID NO 6
<211> LENGTH: 17
<212> TYPE: PRT
<213> ORGANISM: Artificial
<220> FEATURE:
<223> OTHER INFORMATION: Description of artificial sequence:
      Antimicrobial peptide

<400> SEQUENCE: 6

Val Ala Lys Lys Leu Ala Lys Leu Ala Lys Leu Ala Lys Leu Ala
1               5                   10                  15

Leu

<210> SEQ ID NO 7
<211> LENGTH: 13
<212> TYPE: PRT
<213> ORGANISM: Artificial
<220> FEATURE:
<223> OTHER INFORMATION: Description of artificial sequence:
      Antimicrobial peptide

<400> SEQUENCE: 7

Phe Ala Lys Leu Leu Ala Lys Ala Leu Lys Lys Leu Leu
1               5                   10

<210> SEQ ID NO 8
<211> LENGTH: 16
<212> TYPE: PRT
<213> ORGANISM: Artificial
<220> FEATURE:
<223> OTHER INFORMATION: Description of artificial sequence:
      Antimicrobial peptide

<400> SEQUENCE: 8

Lys Gly Leu Lys Lys Gly Leu Lys Leu Leu Lys Lys Leu Leu Lys Leu
1               5                   10                  15

<210> SEQ ID NO 9
<211> LENGTH: 16
<212> TYPE: PRT
<213> ORGANISM: Artificial
<220> FEATURE:
<223> OTHER INFORMATION: Description of artificial sequence:
      Antimicrobial peptide

<400> SEQUENCE: 9

Lys Gly Leu Lys Lys Leu Leu Lys Leu Gly Lys Lys Leu Leu Lys Leu
1               5                   10                  15

<210> SEQ ID NO 10
<211> LENGTH: 16
<212> TYPE: PRT
<213> ORGANISM: Artificial
<220> FEATURE:
<223> OTHER INFORMATION: Description of artificial sequence:
      Antimicrobial peptide

<400> SEQUENCE: 10

Lys Gly Leu Lys Lys Leu Gly Lys Leu Leu Lys Lys Leu Leu Lys Leu
1               5                   10                  15

<210> SEQ ID NO 11
<211> LENGTH: 16
<212> TYPE: PRT
<213> ORGANISM: Artificial
<220> FEATURE:
<223> OTHER INFORMATION: Description of artificial sequence:
      Antimicrobial peptide
```

```
<400> SEQUENCE: 11

Lys Gly Leu Lys Lys Leu Leu Lys Leu Leu Lys Lys Gly Leu Lys Leu
1               5                   10                  15

<210> SEQ ID NO 12
<211> LENGTH: 16
<212> TYPE: PRT
<213> ORGANISM: Artificial
<220> FEATURE:
<223> OTHER INFORMATION: Description of artificial sequence:
      Antimicrobial peptide

<400> SEQUENCE: 12

Lys Gly Leu Lys Lys Leu Leu Lys Leu Leu Lys Lys Leu Gly Lys Leu
1               5                   10                  15

<210> SEQ ID NO 13
<211> LENGTH: 19
<212> TYPE: PRT
<213> ORGANISM: Artificial
<220> FEATURE:
<223> OTHER INFORMATION: Description of artificial sequence:
      Antimicrobial peptide

<400> SEQUENCE: 13

Phe Ala Leu Ala Leu Lys Ala Leu Lys Lys Leu Lys Lys Ala Leu Lys
1               5                   10                  15

Lys Ala Leu

<210> SEQ ID NO 14
<211> LENGTH: 17
<212> TYPE: PRT
<213> ORGANISM: Artificial
<220> FEATURE:
<223> OTHER INFORMATION: Description of artificial sequence:
      Antimicrobial peptide

<400> SEQUENCE: 14

Phe Ala Lys Lys Leu Ala Lys Leu Ala Lys Lys Leu Ala Lys Leu Ala
1               5                   10                  15

Leu

<210> SEQ ID NO 15
<211> LENGTH: 13
<212> TYPE: PRT
<213> ORGANISM: Artificial
<220> FEATURE:
<223> OTHER INFORMATION: Description of artificial sequence:
      Antimicrobial peptide

<400> SEQUENCE: 15

Phe Ala Lys Leu Leu Ala Lys Leu Ala Lys Lys Leu Leu
1               5                   10

<210> SEQ ID NO 16
<211> LENGTH: 15
<212> TYPE: PRT
<213> ORGANISM: Artificial
<220> FEATURE:
<223> OTHER INFORMATION: Description of artificial sequence:
      Antimicrobial peptide

<400> SEQUENCE: 16

Phe Ala Lys Lys Leu Ala Lys Leu Ala Leu Lys Leu Ala Lys Leu
1               5                   10                  15
```

```
<210> SEQ ID NO 17
<211> LENGTH: 10
<212> TYPE: PRT
<213> ORGANISM: Artificial
<220> FEATURE:
<223> OTHER INFORMATION: Description of artificial sequence:
      Antimicrobial peptide

<400> SEQUENCE: 17

Phe Ala Lys Lys Leu Ala Lys Lys Leu Leu
1               5                   10

<210> SEQ ID NO 18
<211> LENGTH: 13
<212> TYPE: PRT
<213> ORGANISM: Artificial
<220> FEATURE:
<223> OTHER INFORMATION: Description of artificial sequence:
      Antimicrobial peptide

<400> SEQUENCE: 18

Phe Ala Lys Leu Leu Ala Lys Leu Ala Lys Lys Val Leu
1               5                   10

<210> SEQ ID NO 19
<211> LENGTH: 13
<212> TYPE: PRT
<213> ORGANISM: Artificial
<220> FEATURE:
<223> OTHER INFORMATION: Description of artificial sequence:
      Antimicrobial peptide

<400> SEQUENCE: 19

Lys Tyr Lys Lys Ala Leu Lys Lys Leu Ala Lys Leu Leu
1               5                   10

<210> SEQ ID NO 20
<211> LENGTH: 12
<212> TYPE: PRT
<213> ORGANISM: Artificial
<220> FEATURE:
<223> OTHER INFORMATION: Description of artificial sequence:
      Antimicrobial peptide

<400> SEQUENCE: 20

Phe Ala Leu Leu Lys Ala Leu Leu Lys Lys Ala Leu
1               5                   10

<210> SEQ ID NO 21
<211> LENGTH: 14
<212> TYPE: PRT
<213> ORGANISM: Artificial
<220> FEATURE:
<223> OTHER INFORMATION: Description of artificial sequence:
      Antimicrobial peptide

<400> SEQUENCE: 21

Lys Arg Leu Phe Lys Lys Leu Lys Phe Ser Leu Arg Lys Tyr
1               5                   10

<210> SEQ ID NO 22
<211> LENGTH: 14
<212> TYPE: PRT
<213> ORGANISM: Artificial
<220> FEATURE:
<223> OTHER INFORMATION: Description of artificial sequence:
      Antimicrobial peptide
```

```
<400> SEQUENCE: 22

Lys Arg Leu Phe Lys Lys Leu Leu Phe Ser Leu Arg Lys Tyr
1               5                   10

<210> SEQ ID NO 23
<211> LENGTH: 14
<212> TYPE: PRT
<213> ORGANISM: Artificial
<220> FEATURE:
<223> OTHER INFORMATION: Description of artificial sequence:
      Antimicrobial peptide

<400> SEQUENCE: 23

Leu Leu Leu Phe Leu Leu Lys Lys Arg Lys Lys Arg Lys Tyr
1               5                   10

<210> SEQ ID NO 24
<211> LENGTH: 36
<212> TYPE: PRT
<213> ORGANISM: Hyalophora cecropia

<400> SEQUENCE: 24

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Trp Gly Gln Ala Thr
            20                  25                  30

Gln Ile Ala Lys
        35

<210> SEQ ID NO 25
<211> LENGTH: 23
<212> TYPE: PRT
<213> ORGANISM: Xenopus sp.

<400> SEQUENCE: 25

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 26
<211> LENGTH: 22
<212> TYPE: PRT
<213> ORGANISM: Xenopus sp.

<400> SEQUENCE: 26

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 27
<211> LENGTH: 12
<212> TYPE: PRT
<213> ORGANISM: Bos taurus

<400> SEQUENCE: 27

Arg Leu Cys Arg Ile Val Val Ile Arg Val Cys Arg
1               5                   10
```

-continued

```
<210> SEQ ID NO 28
<211> LENGTH: 13
<212> TYPE: PRT
<213> ORGANISM: Bos sp.

<400> SEQUENCE: 28

Ile Leu Pro Trp Lys Trp Pro Trp Trp Pro Trp Arg Arg
1               5                   10

<210> SEQ ID NO 29
<211> LENGTH: 24
<212> TYPE: PRT
<213> ORGANISM: Homo sapiens

<400> SEQUENCE: 29

Asp Ser His Ala Lys Arg His His Gly Tyr Lys Arg Lys Phe His Glu
1               5                   10                  15

Lys His His Ser His Arg Gly Tyr
            20
```

PROCESS FOR PROVIDING ANTIMICROBIAL SURFACES

FIELD OF INVENTION

This invention relates to polymer chemistry and modification of polymer surfaces to provide antimicrobial surfaces.

BACKGROUND OF INVENTION

Medical device related microbial infections pose serious clinical and economic costs. One mechanism for reducing these costs and potentially serious negative health outcomes, is to provide antimicrobial coatings on medical devices. Antimicrobial coatings for biomedical devices have been described. For example, coatings containing antibiotics, quaternary ammonium compounds, and silver have been described. However, use of these coatings, particularly on medical devices, has disadvantages. For instance, the use of antibiotic coatings may lead to the development of antibiotic resistant microorganisms and quaternary ammonium compounds often elicit irritancy. There exists a need for safe and effective antimicrobial surfaces applied to medical devices.

Moreover, there are many other products or articles in which an antimicrobial surface or coating would be beneficial. These include, in addition to medical devices, non-woven fabric, fiber, films and barrier materials such as wound dressings, surgical gowns, gloves, aprons, and drapes.

Antimicrobial peptides (AMPs) are ubiquitous in nature and play an important role in the innate immune system of many species (Zasloff, M., Nature (2002) 415:389-395; Epand, R. M., and Vogel, H. J., Biochim Biophys Acta (1999) 1462:11-28). Antimicrobial peptides are diverse in structure, function, and specificity. The structure of AMPs can be divided into two classes: linear peptides with no cysteine residues, and peptides with cysteine residues which contain one or multiple disulfide bonds. These structurally diverse AMPs share a common structural motif in that they are often cationic and amphiphilic. Amphiphilic peptides are characterized by spatially segregated polar and non-polar residues. It is believed that the cationic amphiphilic AMPs interact with the negatively charged bacterial cell membrane. The interaction of antimicrobial peptides with bacteria is thought to produce membrane perturbations, leading to rapid cell death (Shai, Y., Biochim Biophys Acta (1999) 1462:55-70; Matsuzaki, K., Biochim Biophys Acta (1999) 1462:1-10; Yang, et al. Biophys. J. (2000) 79:2002-2009). Due to the non-specific mode of action of antimicrobial peptides, resistance to the antimicrobial peptides is thought to be less likely than antibiotics that act on specific targets (Zasloff, supra; Epand, supra).

WO2002/064183 discloses biomedical devices with antimicrobial cationic peptide and protein coatings. In particular, contact lenses coated with protamine, melittin, cepropin A, nisin, or a combination thereof, exhibited antimicrobial properties. The coating process involved contacting the lens material with a solution of antimicrobial peptides.

WO2004/056402 discloses a coated biomedical device wherein the device contained a latent reactive component coated with a peptide containing coating.

WO2004/056407 discloses biomedical devices with antimicrobial coatings. In particular, contact lenses coated with L-melimine, protamine or combinations thereof, reduce by greater than about 50 percent, either or both, the number of bacteria adhering to the surface and the growth of bacteria adhering to the surface.

U.S. Pat. No. 5,847,047 describes compositions containing polymer-bound oligopeptides. According to this reference, cationic oligopeptides comprised of leucine and lysine residues exhibited antimicrobial activity when bound to polymeric materials.

Reaction of polyamides with formaldehyde is known. Lin et. al. described the reaction of nylon with aqueous formaldehyde under basic condition (Jian Lin, Catherine Winkelman, S. D. Worley, R. M. Broughton, J. E. Williams, *J. Appl. Poly. Science*, 81, 943-947 (2001). U.S. Pat. No. 4,182,695 discloses the bonding of biologically active proteins on polyamides by first reaction of polyamide with formaldehyde and a compound condensable with formaldehyde that contains at least one further reactive group, and reacting the product with a protein.

Functionalization of amides, lactams, and imides with formaldehyde, and further reaction of the hydroxymethyl intermediate under the action of hydrogen halide, thionyl chloride, or a phosphorous halide is known (H. E. Zaugg and W. B. Martin, Org. React., 14, 52 (1965)). An alternate procedure utilizing halosilanes in the synthesis of N-(halomethyl) derivatives of lactams, N-methylcarboxyamides, and imides is described by Orlova, N. A. et. al (N. A. Orlova, A. G. Shipov, I. A. Savost'yanova, Yu. I. Baukov, Russian Journal of general chemistry (English trans) EN: 61, 9.2; 1991; 1875-1881.)

Applicants have found processes for providing durable antimicrobial surfaces that include treating a polymer substrate with formaldehyde followed by treatment with an antimicrobial peptide.

SUMMARY OF INVENTION

One embodiment of the invention is a process for providing a durable antimicrobial surface on a polymer substrate comprising: a) treating a polymer substrate with a first fluid comprising formaldehyde and a co-reactant selected from the group: acid, anhydride, reactive halide, and mixtures thereof; wherein the formaldehyde and co-reactant are present in amounts effective to provide a polymer substrate with a chemically modified surface; and b) treating the chemically modified surface with an antimicrobial fluid comprising an effective amount of an antimicrobial peptide sufficient to provide a durable antimicrobial surface.

Another embodiment of the invention is a process for providing a durable antimicrobial surface on a polymer substrate comprising: a) (1) treating a polymer substrate with a first alternative fluid comprising formaldehyde and a hydroxymethylation catalyst wherein the formaldehyde and hydroxymethylation catalyst are present in an amount effective to provide a polymer substrate with a hydroxymethyl surface; a) (2) treating the hydroxymethyl surface with a second alternative fluid comprising a reactant selected from the group: acid, anhydride, reactive halide, and mixtures thereof; in an amount effective to provide a polymer substrate with a chemically modified surface; and (b) treating the chemically modified surface, with an antimicrobial fluid comprising an effective amount of an antimicrobial peptide sufficient to provide a durable antimicrobial surface.

Other embodiments of the invention are articles characterized by a durable antimicrobial surface provided by the process of the invention.

DETAILED DESCRIPTION OF INVENTION

The polymer substrate that is the subject of modification in the invention includes the surface of a polymer article, film, bead, fiber, nonwoven and woven fabric, and coating. The polymer substrate also encompasses a non-polymer article, film, etc., such as a metal or composite article, or other material or device, that is coated with a polymer coating. Preferably the substrate comprises one or more polymers, homopolymers, copolymers, block copolymers and graft polymers selected from the group: polyamide, polyurethane, and polyurea.

Polyamide refers to the homopolymers to which belong the polycondensates of ω-aminocarboxylic acids and the polycondensates of linear aliphatic diamines and dicarboxylic acids, as well as the polycondensates with aromatic or other components; and to copolyamides that may be a random mixture of polycondensates or a polycondensate of a mixture of homopolymer segments that results in a block copolymer. Typical examples include polycaprolactam, polycondensates of adipic acid and hexamethylenediamine (6.6-polyamide), 6,10-polyamide, polyaminoundecanoic acid, and mixed polyamides of caprolactam and dicarboxylic acid diamine salts, such as adipic acid 4,4'-diaminodicyclohexylmethane.

Polyurethane refers to the polymers, homopolymers and copolymers resulting from the polycondensation of one or more diisocyanates with one or more diols or polyols. Herein the term copolymer refers to a polymer that is made up of two or more repeat units. Because of the nature of the polymerization process, the term polyurethane also encompasses polycondensates having a certain amount of urea and ureido moieties.

The diisocyanates useful in the polycondensation to form polyurethanes include diisocyanates selected from the group consisting of isophorone diisocyanate, 5-isocyanato-1-(2-isocyanatoeth-1-yl)-1,3,3-trimethylcyclohexane, 5-isocyanato-1-(3-isocyanatoprop-1-yl)-1-yl)-1,3,3-trimethylcyclohexane, 5-isocyanato-(4-isocyanatobut-1-yl) -1,3,3-trimethylcyclohexane, 1-isocyanato-2-(3-isocyanatoprop-1-yl) cyclohexane, 1-isocyanato-2-(3-isocyanatoeth-1-yl) cyclohexane, 1-isocyanato-2-(4-isocyanatobut-1-yl) cyclohexane, 1,2-diisocyanatocyclobutane, 1,3-diisocyanatocyclobutane, 1,2-diisocyanatocyclopentane, 1,3-diisocyanatocyclopentane, 1,2-diisocyanatocyclohexane, 1,3-diisocyanatocyclohexane, 1,4-diisocyanatocyclohexane, dicyclohexylmethane 2,4'-diisocyanate, trimethylene diisocyanate, tetramethylene diisocyanate, pentamethylene diisocyanate, hexamethylene diisocyanate, ethylethylene diisocyanate, trimethylhexane diisocyanate, heptamethylene diisocyanate, 2-heptyl-3,4-bis(9-isocyanatononyl)-1-pentylcyclohexane, 1,2-, 1,4-, and 1,3-bis(isocyanatomethyl)cyclohexane, 1,2-, 1,4-, and 1,3-bis(2-isocyanatoeth-1-yl)cyclohexane, 1,3-bis(3-isocyanatoprop-1-yl) cyclohexane, 1,2-, 1,4- or 1,3-bis(4-isocyanatobut-1-yl) cyclohexane, liquid bis(4-isocyanatocyclohexyl)methane with a trans/trans content of up to 30% by weight, toluene diisocyanate, xylylene diisocyanate, bisphenylene diisocyanate, methylene bis(p-phenyl isocyanate) (MDI), naphthylene diisocyanate, and combinations thereof.

The diols and polyols useful in the polycondensation to form polyurethanes include ethylene glycol, 1,2- or 1,3-propanediol, 1,2-, 1,3- or 1,4-butanediol, 1,2-, 1,3-, 1,4- or 1,5-pentanediol, 1,2-, 1,3-, 1,4-, 1,5- or 1,6-hexanediol, neopentyl hydroxypivalate, neopentyl glycol, diethylene glycol, 1,2-, 1,3- or 1,4-cyclohexanediol, 1,2-, 1,3- or 1,4-cyclohexanedimethanol, trimethylpentanediol, ethylbutylpropanediol, the positionally isomeric diethyloctanediols, 2-butyl-2-ethyl-1,3-propanediol, 2-butyl-2-methyl-1,3-propanediol, 2-phenyl-2-methyl-1,3-propanediol, 2-propyl-2-ethyl-1,3-propanediol, 2-di-tert-butyl-1,3-propanediol, 2-butyl-2-propyl-1,3-propanediol, 1-dihydroxymethylbicyclo[2.2.1]heptane, 2,2-diethyl-1,3-propanediol, 2,2-dipropyl-1,3-propanediol, 2-cyclohexyl-2-methyl-1,3-propanediol, 2,5-dimethyl-2,5-hexanediol, 2,5-diethyl-2,5-hexanediol, 2-ethyl-5-methyl-2,5-hexanediol, 2,4-dimethyl-2,4-pentanediol, 2,3-dimethyl-2,3-butanediol, 1,4-bis(2'-hydroxypropyl)benzene, 1,3-bis(2'-hydroxypropyl)benzene and polytetramethylene oxide (PTMO); ester diols such as δ-hydroxybutyl-ε-hydroxy-caproic esters, ω-hydroxyhexyl-γ-hydroxybutyric esters, adipic acid β-hydroxyethyl esters and terephthalic acid bis(β-hydroxyethyl) ester; and in minor amounts trimethylolethane, trimethylolpropane, glycerol, pyrocatechol, resorcinol, hydroquinone, pyrogallol, phloroglucinol and hydroxyhydroquinone. Of these diols and polyols, polytetramethylene oxide is particularly advantageous in formation of polyurethanes useful as substrates in the invention. Further diols and polyols useful in the polycondensation to form polyurethanes are polysiloxane polyols; and polyester polyols, polycarbonate polyols, and polyether polyols disclosed in U.S. Pat. No. 6,927,254, hereby incorporated by reference.

Thermoplastic polyurethanes that are especially useful and preferred as substrates in the invention have a block, or segmented, structure, comprising a hard, high-melting segment, copolymerized with a soft rubbery segment, resulting in a thermoplastic polyurethane elastomer. At room temperature, the liquid-like soft blocks are strengthened and reinforced by the hard blocks or segments. At elevated temperatures, the hard blocks soften and flow to permit thermoplastic processing. Upon cooling, the original structure reforms. Physical characteristics and methods for preparing thermoplastic polyurethane elastomers are disclosed in U.S. Pat. No. 5,589,563, hereby specifically incorporated by reference. Preferred polyisocyanates for the preparation of the hard segment of thermoplastic polyurethane elastomers are diphenylmethane diisocyanate and dicyclohexylmethanediisocyanate, and mixtures thereof. The molecular weight of the diisocyanate component of the hard segment is preferably about 100 to about 500 and more preferably about 150 to about 270.

A chain extender of the hard segment can be used in preparation of the polyurethane elastomers useful in the invention may be an aliphatic polyol as defined above or a polyamine such as is known for preparing polyurethanes.

Preferred polyols for the hard segment are 1,4-butanediol, ethylene glycol, 1,6-hexanediol, glycerine, trimethylolpropane, pentaerythritol, 1,4-cyclohexane dimethanol, phenyldiethanolamine, and mixtures thereof, among others. Other polyols are also suitable.

The hard segment of the thermoplastic polyurethane elastomers useful in the invention may contain urea linkages resulting from condensation of a polyamine with the diisocyanates. The polyamine of the hard segment may be selected from the group consisting of alkyl, cycloalkyl, and aryl amines which may be further substituted with nitrogen, oxygen, or halogen, complexes thereof with alkali metal salts, and mixtures thereof. Suitable polyamines for preparing the hard segment are p,p'-methylenedianiline and complexes thereof with alkali metal chlorides, bromides, iodides, nitrites, and nitrates, 4,4'-methylene-bis(2-chloroaniline), piperazine, 2-methylpiperazine, oxydianiline, hydrazine, ethylenediamine, cyclohexanediamine, xylylenediamine, bis (p-aminocyclohexyl)methane, the dimethyl ester of 4,4'-methylenedianthranilic acid, p-phenylenediamine, o-phenylenediamine, 4,4'-methylenebis(2-methoxyaniline), 4,4'-methylenebis(N-methylaniline), 2,4-toluenediamine, 2,6-toluenediamine, benzidine, dichlorobenzidine, 3,3'-dimethylbenzidine, 3,3'-dimethoxybenzidine, dianisidine, 1,3-propanediol bis(p-aminobenzoate), isophorone diamine, and mixtures thereof. Particularly convenient polyamine mixtures are of ethylenediamine and 1,3-cyclohexanediamine.

The soft segment used in the preparation of the polyurethane elastomers useful in the invention may be a polyfunctional aliphatic polyol, or a polyfunctional aliphatic or aromatic amine, such as are commonly used for the preparation of polyurethanes or mixtures thereof.

The aliphatic polyols of the soft segment may be selected from the group consisting of linear and branched polyalkylene and polyalkenyl oxides, random and block copolymers thereof, polycarbonate polyols, hydroxyl-terminated silicones, random and block copolymers thereof with polyalkylene oxides, linear and branched polyalkenyl and polyalkylene polyols, and mixtures thereof. However, other polyols may also be utilized if the resultant polymer possesses the required bulk properties, e.g. tensile strength. Examples of polyols that are suitable for polyurethane elastomers useful in the invention are polyethylene oxides, polypropyleneoxides, polytetramethylene oxides (PTMO), random or block polypropylene oxide-polyethylene oxide copolymers, various ethyleneoxide-terminated polyols, random or block polytetramethylene oxide-polyethylene oxide copolymers, polycarbonate diols and triols, multifunctional hydroxyalkyl- or amine-terminated silicones, random or block silicone-polyethyleneoxide copolymers, polybutadiene diols and triols, polyisobutylene diols and triols, polybutylene oxide diols and triols, and mixtures thereof. A preferred polyol is PTMO.

The amines of the soft segment may be selected from the group consisting of amine-terminated homologues of the exemplary polyols, including but not limited to polyamine-terminated alkylene oxides and random and block copolymers thereof, polyamine-terminated silicones, random and block copolymers thereof with polyalkylene oxides and mixtures thereof. Examples of the amines that are suitable for use in the present invention are multifunctional amine-terminated polytetramethylene oxides, multifunctional amine terminated polyethylene oxides, random or block multifunctional amine terminated polypropylene oxide-polyethylene oxide copolymers, random or block multifunctional amine-terminated polytetramethylene oxide-polyethylene oxide copolymers, multifunctional amine-terminated silicones, random or block amine-terminated silicon polyethylene oxide copolymers and mixtures thereof.

Polyurea refers to the homopolymers and copolymers resulting from the polycondensation of one or more diisocyanates with one or more diamines. Because of the nature of the polymerization process, the term polyurea also encompasses polycondensates having a certain amount of ureido moieties. The diisocyanates useful in the polycondensation to form polyureas are as described above. The diamines useful in the polycondensation to form polyureas include the diamines and diamine salts described above.

Polyurethanes and polyureas also refers to urethane-urea copolymers encompassing a mixture of urethane and urea repeat units, either in a random or a blocky sequence. The urethane-urea copolymers result from the polycondensation of one or more diisocyanates with one or more diamines and one or more diols or polyols.

The formaldehyde used in the processes of the invention refers to the usual forms of formaldehyde, i.e., aqueous formaldehyde solutions commonly referred to as formalin; and paraformaldehyde and trioxane, which, upon dissolution or heating, liberate formaldehyde. A preferred form of formaldehyde for use in the invention is paraformaldehyde.

As used herein, the term "about" modifying the quantity of an ingredient, reactant or reaction condition of the invention or employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about", the claims include equivalents to the quantities.

A first embodiment of the invention comprises a one step process to provide a chemically modified surface suitable for reaction with an antimicrobial peptide. In step (a) of the first embodiment the polymer substrate is treated with a first fluid comprising formaldehyde and a co-reactant to provide a chemically modified surface. The co-reactant useful in step (a) of the first embodiment is selected from the group: acid, anhydride, reactive halide, and mixtures thereof. Acid and anhydride include those compounds conventionally termed acids and anhydrides and include mineral acids, for instance, hydrogen chloride, hydrogen bromide, hydrogen iodide, sulfuric acid, phosphoric acid; acetic anhydride and higher homologs, inorganic anhydrides, for example phosphorous pentoxide, and mixed anhydrides including formic-acetic anhydride. Reactive halide refers to those compounds conventionally termed acid halides, including acetyl chloride, thionyl chloride, phosphorous chloride, phosphorous oxychloride and the like; and reactive organohalides including trimethylsilylchloride, trimethylsilylbromide, and trimethylsilyliodide. Preferred co-reactants are selected from the group: trimethylsilylchloride, trimethylsilylbromide and hydrogen chloride; and trimethylsilylchloride is a most preferred co-reactant.

The polymer substrate may be treated in step (a) of the first embodiment with the first fluid in a variety of ways, including: immersing the substrate in the fluid; coating the substrate surface by, for instance, a spray, curtain, or knife-blade coating process; printing the fluid in a uniform or patterned process; or any other convenient method for applying the fluid to the surface of the polymer substrate. Preferably, the polymer substrate is immersed in the fluid.

The first fluid can be in the form of a liquid, gas, or supercritical fluid. In a preferred embodiment the fluid is a liquid at room temperature and ambient pressure. The fluid may or may not comprise a solvent as a carrier for the formaldehyde and the co-reactant. The solvent, preferably, should not dissolve the polymer substrate surface. General families of solvents useful in step (a) of the first embodiment include: water, tetrahydrofuran, dioxane, halogenated hydrocarbons such as dichloromethane, chloroform, and 1,2-dichloroethane, and aliphatic and aromatic hydrocarbons. Other solvents include supercritical carbon dioxide and other gases commonly used in supercritical processing. In a preferred embodiment, no solvent is used and the first fluid consists essentially of formaldehyde, in the form of paraformaldehyde, and trimethylsilylchloride.

The reaction parameters for step (a) of the first embodiment can be in a range that allows processing in any fluid state. Typically, the reaction temperature is about 4° C. to about 100° C., and the reaction pressure is ambient pressure to about 3 atm. Preferably the reaction temperature is about 25° C. to about 60° C. and, more preferably, about 40 to about 55° C.; and the reaction pressure is ambient pressure. The reaction time can be from 0.1 to about 24 h, preferably, about 0.1 h to about 12 h, and more preferably, about 0.1 h to about 4 h. The concentration of formaldehyde can be about 0.0005 to about 10 mol/L, and preferably about 0.01 to about 1.0 mol/L. Preferably the co-reactant is the fluid phase. However, in cases wherein a solvent is used, the concentration of co-reactant can be about 0.0005 to about 10 mol/L, and preferably, about 0.1 to about 1.0 mol/L.

After treating the polymer substrate to provide a chemically modified surface on polymer substrate, the chemically modified surface can be, optionally, washed or rinsed with one or more wash solvents to remove formaldehyde, co-reactant and by-products of step (a). Wash solvents can be of a wide variety. However, preferred wash solvents are those wherein the polymer substrate surface and/or chemically modified surface, remain insoluble. Typical wash solvents include acetonitrile, lower aliphatic alcohols, aromatic and aliphatic hydrocarbon, water, and combinations thereof.

Not wishing to be bound by any theory, the applicants offer the following explanation as a means to understand the chemical transformation in step (a) of the first embodiment of the invention. It is thought that surface N—H groups related to the polyurethane, polyamide or polyurea may undergo reaction with formaldehyde and a co-reactant, described above, to provide an N-substituted functionality according to the following equation:

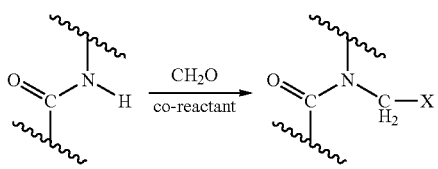

wherein X = Cl, Br, I, OAc, etc.

A second embodiment of the invention comprises a two step process to provide a chemically modified surface suitable for reaction with an antimicrobial peptide. In step (a) (1) of the second embodiment the polymer substrate surface is treated with a first alternative fluid comprising an effective amount of formaldehyde, and a hydroxymethylation catalyst; sufficient to provide a polymer substrate with a hydroxymethyl modified surface.

Hydroxymethylation catalyst refers to an acid or base capable of catalyzing the addition of formaldehyde to an N—H bond of an amide, urethane or urea group. Typical catalysts include mineral acids, for instance, hydrogen chloride, hydrogen bromide, hydrogen iodide; sulfuric acid, glacial acetic acid, formic acid, and mixtures thereof. Typical base catalysts that act as hydroxymethylation catalysts include alkali metal carbonates and hydroxides, for instance sodium hydroxide and potassium carbonate.

Typically 0.0001 M to about 0.01 M concentration of catalyst in the first alternative fluid is sufficient to provide the desired effect.

In step (a) (1) of the second embodiment the process parameters are similar to those described for step (a) of the first embodiment. However, the first alternative fluid is preferably an aqueous formaldehyde solution, which may, or may not, contain an organic co-solvent.

After treating the polymer substrate surface to provide a polymer substrate with a hydroxymethyl modified surface, the surface can be, optionally, washed or rinsed with one or more wash solvents to remove formaldehyde, catalyst and by-products of step (a) (1). Useful wash solvents are similar to those described above.

Not wishing to be bound by any theory, in step (a) (1) of the second embodiment, it is thought that surface N—H groups related to the polyurethane, polyamide or polyurea may undergo reaction with formaldehyde in the presence of a hydroxymethylation catalyst, to provide an N-substituted hydroxymethyl functionality according to the following equation:

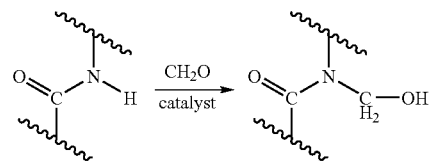

In step (a) (2) of the second embodiment the hydroxymethyl modified surface is treated with a second alternative fluid comprising an effective amount of reactant selected from the group: acid, anhydride, reactive halide, and mixtures thereof; to provide a polymer substrate with a chemically modified surface. The reactant can be any of those described as the co-reactant in step (a) of the first embodiment.

The reaction parameters in step (a) (2) of the second embodiment are the same as described for step (a) of the first embodiment, with the exception that formaldehyde is not required. After performing step (a) (2) of the second embodiment to provide a chemically modified surface, the surface can be, optionally, washed or rinsed with one or more wash solvents to remove reactant and any by-products of step (a) (2). Useful wash solvents are similar to those described above.

Not wishing to be bound by any theory, it is thought that surface hydroxymethyl groups undergo reaction with the reactant, to provide an N-substituted functionality according to the following equation:

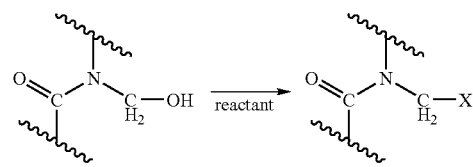

wherein X=Cl, Br, I, OAc, etc.

In step (b) of the invention the chemically modified surface provided by either step (a) of the first embodiment or steps (a) (1) and (a) (2) of the second embodiment is contacted with an antimicrobial fluid comprising an antimicrobial peptide, and optionally a base catalyst, under reaction parameters sufficient to provide a polymer substrate with a durable antimicrobial surface. Again, not wishing to be bound by any theory, the applicants offer the following explanation as a means to understand the chemical transformation in step (b) of the embodiments of the invention. It is thought that chemically modified surface groups undergo a reaction with the antimicrobial peptide to provide a surface bonded peptide according to the following equation:

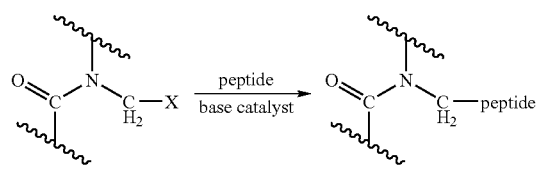

Antimicrobial peptides useful in the present invention are naturally derived or synthetic antimicrobial peptides. The antimicrobial peptides include linear peptides, disulfide containing peptides, peptides with thio-ether rings, and peptaibols which are peptides containing a large proportion of α-amino-isobutyric acid residues. The preferred antimicrobial peptides useful in the invention are characterized by a weight average molecular weight of about 1,000 to about 60,000 Daltons, preferably have no more than 40 amino acid residues, and contain a net positive charge of greater than 1 at physiological pH. The peptides can have an acid C-terminus (—$CO_2H$) or an amide C-terminus (—$CONH_2$).

The more preferred antimicrobial peptides are linear peptides. The more preferred antimicrobial peptides consist essentially of, or consist of, phenylalanine, leucine, isoleucine, valine, alanine, lysine, and arginine residues. The more preferred antimicrobial peptides have a percent amino acid composition of phenylalanine, leucine, isoleucine, valine, alanine, lysine, and arginine residues of at least 50%, 55%, 60%, 65%, 70%, 75%, 80%, 85%, 90%, 95%, or 100%.

The antimicrobial peptides used in the present invention include naturally occurring peptides described in the references: Zasloff, M., Nature (2002) 415:389-395; and Epand, R. M., and Vogel, H. J., Biochim Biophys Acta (1999) 1462: 11-28. These peptides often include amine and thiol groups that may react with the chemically modified polymer in the process of the invention. The naturally occurring antimicrobial peptides are diverse in structure. Some examples of naturally occuring antimicrobial peptides in the present invention are: linear α-helical antimicrobial peptides such as protamine, cecropin A (isolated from the cepropia moth), melittin (bee venom), nisin, magainins (from frog skin), linear non-α-helical peptides such as indolicidin, histatin, one disulfide bond peptide such as brevinin, and multiple disulfide bonded peptides such as α-defensin, β-defensin, drosomycin. The naturally occurring peptides have served as starting points for the design of synthetic peptide analogs.

Other peptides useful in the invention include synthetic peptides. In one embodiment, the antimicrobial peptides useful in the present invention are α-helical amphiphilic cationic peptides, wherein in the α-helical conformation, the peptides are characterized by having a majority of the hydrophobic residues on one side of the helix and the majority of cationic residues on the opposite side. These peptides exhibit lateral amphiphilicity. Some examples of this class of antimicrobial peptides are disclosed by DeGrado et al. (J. Am. Chem. Soc. (1981) 103:679-681). WO9201462, WO2005019241, EP1174027a1, and US20030109452, hereby incorporated by reference, provide further examples of synthetic amphiphilic cationic antimicrobial peptides.

In one embodiment, the antimicrobial peptides useful in the present invention are α-helical amphiphilic cationic peptides, wherein in the α-helical conformation, the peptides are characterized by having a majority of the hydrophobic residues on top, and the majority of cationic residues on the bottom. These peptides are said to exhibit longitudinal amphiphilicity.

In one embodiment, the antimicrobial peptides are amphiphilic β-strand peptides. The preferred β-strand conformation has a maximum hydrophobic moment at 180° as disclosed in the reference: D. Eisenburg, E. Schwartz, M. Komaromy, and R. Wall, J. Mol. Biol., 179, 125-142 (1984). The peptides have the hydrophobic residues on the left and the hydrophophilic/cationic residues on the right or vice versa.

In one embodiment, the antimicrobial peptides are linear, non-α-helical and non-β-strand.

In one embodiment, the antimicrobial peptides contain both L, D-diastereomers of the naturally occurring amino acids. The preferred specific peptide sequences for the invention are listed in Table 1.

Table 1. Sequence of preferred peptides.
Sequence

| No. | Name | Primary sequence |
|---|---|---|
| 1 | PG1 | PKGLKKLLKGLKKLLKL |
| 2 | G1 | KGLKKLLKGLKKLLKL |
| 3 | | KGLKKLLKLLKKLLKL |
| 4 | | LKKLLKLLKKLLKL |
| 5 | | LKKLLKLLKKLL |
| 6 | P50 | VAKKLAKLAKKLAKLAL |
| 7 | P55 | FAKLLAKALKKLL |
| 8 | | KGLKKGLKLLKKLLKL |
| 9 | | KGLKKLLKLGKKLLKL |
| 10 | | KGLKKLGKLLKKLLKL |
| 11 | | KGLKKLLKLLKKGLKL |
| 12 | | KGLKKLLKLLKKLGKL |
| 13 | | FALALKALKKLKKALKKAL |
| 14 | | FAKKLAKLAKKLAKLAL |
| 15 | | FAKLLAKLAKKLL |
| 16 | | FAKKLAKLALKLAKL |
| 17 | | FAKKLAKKLL |
| 18 | | FAKLLAKLAKKVL |
| 19 | | KYKKALKKLAKLL |
| 20 | | FALLKALLKKAL |
| 21 | | KRLFKKLKFSLRKY |
| 22 | | KRLFKKLLFSLRKY |
| 23 | | LLLFLLKKRKKRKY |
| 24 | cecropin A | KWKLFKKIEKVGQNIRDGIIKAGPAVAWGQATQIAK |
| 25 | Maiganin | GIGKFLHSAKKFGKAFVGEIMNS |
| 26 | | GIGKFLKKAKKFGKAFVKILKK |
| 27 | Bactenecin 1 | RLCRIVVIRVCR |
| 26 | Indolin-cidin | ILPWKWPWWPWRR |
| 29 | Histatin 5 | DSHAKRHHGYKRKFHEKHHSHRGY |

The base catalyst, optionally used in step (b) of the embodiments of the invention can be a variety of inorganic bases such as alkali metal carbonates and hydroxides and organic nitrogen bases lacking a reactive N—H bond. Preferred base catalysts are selected from the group: potassium hydroxide, sodium hydroxide, potassium carbonate, sodium carbonate, trimethylamine, triethylamine, tripropylamine, diisopropylethylamine and tributyl amine.

The antimicrobial fluid preferably, comprises a suitable solvent for both the antimicrobial peptide and the optional base catalyst. In addition, preferred solvents for the antimicrobial fluid are those wherein the chemically modified surface remains insoluble. Typical classes of solvents for the antimicrobial fluid include: water, lower alkyl alcohols, esters and lactones, acids, ethers, ketones, aromatic and aliphatic hydrocarbons, and halogenated aromatic and aliphatic hydrocarbons, or mixtures thereof wherein the chemically modified surface remains insoluble. Preferred solvents for the antimicrobial fluid are selected from the group: water and acetonitrile and mixtures there.

The chemically modified surface may be treated with the antimicrobial fluid in a variety of ways, including: immersing the surface in the second fluid; coating the substrate surface by, for instance, a spray, curtain, or knife-blade coating process; printing the fluid in a uniform or patterned process; or any other convenient method for applying the fluid to the chemically modified surface. Preferably, the chemically modified surface is immersed in the antimicrobial fluid. In another embodiment the chemically modified surface is preferably spray coated with the antimicrobial fluid.

The reaction parameters for the step (b) of the embodiments of the invention can be in a range that allows processing in any fluid state. Typically, the reaction temperature is about 4° C. to about 100° C., and the reaction pressure is ambient pressure. Preferably the reaction temperature is about 25° C. to about 80° C. The reaction time can be from 0.1 to about 24 h, preferably, about 0.1 h to about 10 h, and more preferably, about 0.1 h to about 4 h. The concentration of the antimicrobial peptide can be about $1\times10^{-6}$ to about 0.1 mol/L, and preferably about $1\times10^{-4}$ to about 0.01 mol/L. Preferably the optional base is present in a concentration of about $1\times10^{-6}$ to about 0.1 mol/L, and preferably, about $1\times10^{-4}$ to about 0.01 mol/L.

After contacting the chemically modified surface with the antimicrobial fluid to provide an antimicrobial surface, the surface can be, optionally, washed or rinsed with one or more wash solvents to remove excess antimicrobial peptide, the base, if used, and any byproducts. Preferred wash solvents are of a wide variety. However, preferred wash solvents are those wherein the antimicrobial surface provided by the process remains insoluble. Typical wash solvents include acetonitrile, lower aliphatic alcohols, water, and combinations thereof.

Determination of antimicrobial activity of the polymer substrate with the antimicrobial surface can be accomplished by standard techniques. For the purposes of the present invention, antibacterial activity of the surface was assessed using either a suspended coupon assay or a mini-shake flask test (MSFT).

A comparison of antimicrobial activity of the antimicrobial surfaces provided by the invention to that of simple coatings of antimicrobial peptides on polymer substrates demonstrated the durability of the antimicrobial surfaces provided by the invention. Examples 2A and 2C exhibited significant drops in the number of colony forming units after treatment with the process of the invention, followed by thoroughly washing the samples with wash solvent. Examples 2D and 2E, wherein the same coupons were treated with antimicrobial fluid without first chemically modifying the surface exhibited no decrease in the number of colony forming units, after thoroughly washing the samples with wash solvent.

The process of the invention is useful for providing antimicrobial coatings for a variety of biomedical products including: catheters, pacemaker leads, vascular grafts, blood tubings, balloons, shunts, cardiac-assist devices, urological implants, wound dressings, and barrier materials such as surgical gowns, and drapes.

Applicants specifically incorporate the entire contents of all cited references in this disclosure. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

EXAMPLES

The following examples are provided to demonstrate preferred aspects of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

This example illustrates the formation of an antimicrobial surface on a polycarbonate polyurethane (PC-PU) copolymer film substrate using paraformaldehyde and chlorotrimethylsilane to provide the chemically modified surface.

PC-PU films (2×2 cm, 1 mil thickness, ChronoFlex® C, available from CardioTech International, Inc. Wilmington, Mass.) were immersed in a stirred suspension of paraformaldehyde (0.75 g) and chlorotrimethylsilane (7.2 g). The suspension was heated to 50° C. for 1 h with stirring under reflux. The mixture was allowed to cool. The films were removed and washed, consecutively, with acetonitrile, isopropanol, and distilled deionized (dd) water, each solvent 3 times with 5 mL portions, for 5 min with agitation on a laboratory shaker (135 rpm). The films were dried in a vacuum at 60° C. for 1 h.

The chemically modified PC-PU films were immersed in anhydrous acetonitrile (5 mL); antimicrobial peptide P50 (SEQ ID NO: 6: VAKKLAKLAKKLAKLAL-CONH2), 3 mg, available from Multiple Peptide Systems, San Diego, Calif.) and triethylamine (10 μL) were added; and the mixture heated to 50° C. and shaken for 1 h. The PC-PU films were allowed to cool for 15 min; and washed, consecutively, with acetonitrile, isopropanol, and dd water, as described above. The films were dried in a vacuum at 50° C. for 1 h.

Example 2

This example illustrates the formation of an antimicrobial surface on PC-PU coupon substrates (ChronoFlex® C, available from CardioTech International, Inc. Wilmington, Mass.) using paraformaldehyde and chlorotrimethylsilane to provide the chemically modified surface and P50 peptide to provide the antimicrobial surface.

PC-PU coupons (1.3 cm diameter, 0.3 cm thickness; ChronoFlex® C, available from CardioTech International, Inc. Wilmington, Mass.) were treated with paraformaldehyde (2.5 g) and chlorotrimethylsilane (28 mL) as in example 2 with the exception that 30 mL portions of solvent were used in the wash to provide tacky pale yellow chemically modified surfaces. The chemically modified PU coupons were immersed in three different solutions of anhydrous acetonitrile (4.85, 4.95, and 4.985 mL, respectively) and triethylamine (10 μL) and the following series of P50 stock solution (20 mg/mL in dimethylformamide) added:

2A—0.15 mL to provide 3 mg P50,
2B—0.05 mL to provide 1 mg P50,
2C—0.015 mL to provide 0.3 mg P50.

The resulting slightly cloudy mixtures were heated to 50° C. and shaken for 1 h. The coupons were washed as in example 1, and vacuum dried (50° C., 1 h).

Examples 2D and 2E (Comparative)

This example illustrates the lack of efficacy of PC-PU coupons without the chemical modification, but in the presence of an antimicrobial peptide P50.

PC-PU coupons (ChronoFlex® C) were immersed in two different solutions of anhydrous acetonitrile (4.85 and 4.985 mL, respectively) and triethylamine (10 uL) and the following series of P50 stock solution (20 mg/mL in dimethylformamide) added:

2D—0.15 mL to provide 3 mg P50,
2E—0.015 mL to provide 0.3 mg P50

The resulting cloudy mixtures were heated to 50° C. and shaken for 1 hour. The PC-PU coupons were allowed to cool for 15 min, The coupons were washed as in example 1, and vacuum dried (50° C., 1 h).

Example 3

This example illustrates the formation of an antimicrobial surface on a PC-PU coupon substrate using paraformaldehyde and chlorotrimethylsilane to provide the chemically modified surface and PG1 peptide to provide the antimicrobial surface.

PC-PU coupons (ChronoFlex® C) were treated with paraformaldehyde (3.12 g) and chlorotrimethylsilane (35 mL) as in example 2 with the exception that 40 mL portions of solvent were used in the wash to provide tacky pale yellow chemically modified surfaces. The coupons were vacuum dried at 60° C. for 1.5 h. The chemically modified PC-PU coupons were immersed in three different solutions of anhydrous acetonitrile (4.85, 4.95 and 4.985 mL, respectively) and triethylamine (10 uL) and the following series of PG1 (SEQ ID NO: 1: PKGLKKLLKGLKKLLKL), available from Synpep, Inc., Dublin, Calif.) stock solution (20 mg/mL in dimethylformamide) added:

3A—0.15 mL to provide 3 mg PG1,
3B—0.05 mL to provide 1 mg PG1,
3C—0.015 mL to provide 0.3 mg PG1.

The resulting slightly cloudy mixtures were heated to 50° C. and shaken for 1 h. The coupons were washed as in example 1, and vacuum dried (50° C., 1 h).

Example 4

This example illustrates the formation of an antimicrobial surface on PC-PU coupon substrates using paraformaldehyde and chlorotrimethylsilane to provide the chemically modified surface and P50 peptide and an aqueous buffer solution to provide the antimicrobial surface.

PC-PU coupons (ChronoFlex® C) were treated with paraformaldehyde (6.25 g) and chlorotrimethylsilane (70 mL) as in example 2 with the exception that 30 mL portions of solvent were used in the wash to provide tacky, pale yellow, chemically modified surfaces. The coupons were vacuum dried at 60° C. for 2.0 h.

The chemically modified PC-PU coupons were immersed in two different solutions of 0.1 M sodium carbonate buffer (4.985 and 4.95 mL, respectively, pH=7.5) and the following series of P50 stock solution (20 mg/mL in dd water) added:

4A—0.015 mL to provide 0.3 mg P50,
4B—0.05 mL to provide 1 mg P50.

The resulting mixtures were heated to 80° C. and shaken for 1 h. The solutions were decanted, and the coupons washed, consecutively, with dd water (4 times), Triton™ X-100 solution (available from Sigma, St. Louis, Mo.; 0.1 wt %, 2 times) and dd water (three times); each wash with 10 mL portions, with agitation for 0.25 h. The coupons were dried in a vacuum at 60° C. for 1.5 h.

Example 5

This example illustrates the formation of an antimicrobial surface on PC-PU coupon substrates using paraformaldehyde, chlorotrimethylsilane and a co-solvent to provide the chemically modified surface and P50 peptide to provide the antimicrobial surface.

PC-PU coupons (ChronoFlex® C) were treated with a solution of paraformaldehyde (2.5 g), chlorotrimethylsilane (28 mL) and acetic acid (6.0 g) and agitated on a rotary shaker table for 1 h at room temperature. The samples were washed as described in example 1. The samples were dried in air overnight and in vacuum (60° C., 1.5 h) to provide chemically modified surfaces. The remaining chemically modified PC-PU coupons were immersed in a solution of anhydrous acetonitrile (4.95 mL), P50 stock solution (50 μL, 20 mg/mL in dimethylformamide) and triethylamine (10 uL). The cloudy mixture was heated to 50° C. and shaken for 1 h. The solution was decanted, and the coupons washed, consecutively, as described in example 1. The coupons were dried in a vacuum at 60° C. for 14.5 h.

Example 6 of Step (a)

This example illustrates the formation of an antimicrobial surface on a PC-PU coupon substrate using paraformaldehyde and chlorotrimethylsilane to provide the chemically modified surface and PG1 peptide to provide the antimicrobial surface.

PC-PU coupons (ChronoFlex® C) were treated with a solution of paraformaldehyde (6.25 g) and chlorotrimethylsilane (70 mL) at 50° C. for 1 h. The solution was decanted and the coupons washed with acetonitrile, two times, 75 mL portions; isopropanol, 3 times, 30 mL portions; and dd water, 3 times, 30 mL portions; each wash with agitation for 5 min; to provide chemically modified surfaces. The coupons were vacuum dried at 60° C. for 2 h. The remaining chemically modified PC-PU coupons were immersed in anhydrous acetonitrile (4.95 mL) and triethylamine (10 uL) and PG1 stock solution (0.05 mL, 20 mg/mL in dimethylformamide) added. The resulting slightly cloudy mixture was heated to 50° C. and shaken for 5 h. The coupons were washed as in example 1, oven dried (60° C., 1.5 h) and air dried overnight.

Example 7

This example illustrates the formation of an antimicrobial surface on a polyether polyurethane coupon and P55 antimicrobial peptide.

Polyether polyurethane coupons (Elasthane™, purchased from The Polymer Technology Group, Emeryville, Calif.) were treated with a solution of paraformaldehyde (3.2 g) and chlorotrimethylsilane (35 mL) at 50° C. for 3 h. The solution was decanted and the coupons washed with acetonitrile, two times, 75 mL portions; isopropanol, 3 times, 30 mL portions; and dd water, 3 times, 30 mL portions; each wash with agitation for 5 min; to provide chemically modified surfaces. The coupons were vacuum dried at 60° C. for 2 h. The chemically modified PU coupons were immersed in 0.1 M sodium carbonate (3 mL, pH 8.4). P55 antimicrobial peptide (2 mg peptide in 0.3 mL water; antimicrobial peptide P55 (SEQ ID NO: 7: FAKLLAKALKKLL); synthesized by solid phase synthesis and purified to >98% purity by reverse phase high pressure liquid chromatography) was added and resulting slightly cloudy mixture was heated to 80° C. and shaken for 1 h and left at room temperature overnight. The PU coupons was rinsed with water (5 times with 10 mL portions), and shaken in water for 1 hour, and dried in air.

Example 8

This example illustrates the efficacy of the antimicrobial coatings prepared in the earlier examples using a suspended coupon test.

A single colony of *Escherichia coli* ATCC 25922 or other bacterium was inoculated from a trypticase soy agar plate into trypticase soy broth (TSB) and incubated overnight at 37° C. The inoculum for the assay was prepared by diluting an aliquot of the overnight culture 1:100 into 10 mM phosphate buffer, pH 7.4, to achieve a concentration of approximately $5 \times 10^7$ colony forming units (cfu)/ml.

Sample coupons were placed onto a wire hook suspended from the lid of a sterile scintillation vial containing 10 mM phosphate buffer (15 ml) supplemented with M9 glucose media (Difco, Inc.) to a final concentration of 5 wt %. The above inoculum (150 µl) was added, yielding a cell concentration in the bulk fluid of about $5 \times 10^5$ cfu/ml. Cfu/ml in the bulk fluid was determined at the beginning and end of each test. The vials were placed on the orbiting platform of a 37° C. incubator for 6 h. At 6 h the bulk fluid was sampled for viable cfu/ml by removing four 20 µl aliquots and adding them to four 180 µl portions of trypticase soy broth (TSB) in the first column of a 96 well microtitre plate and performing ten-fold serial dilutions across the plate. The plates were incubated overnight at 37° C., scored visually by observing the last well displaying visual growth, and the number of cfu/ml calculated using the Most Probable Number (MPN) method. Antibacterial activity was determined by comparing the concentration of viable bacteria at the end of the incubation as compared to the number present at initiation of the incubation.

Bacteria on the surface of the test coupon were counted by rinsing the coupon gently in 10 mM phosphate buffer, then placing the coupon in the phosphate buffer (5 ml) and cavitating in a sonic bath for 4 min. The fluid was sampled for viable cfu/ml by removing four 40 µl aliquots and adding them to four 160 µl portions of TSB in the first column of a 96 well microtitre plate and performing a five-fold serial dilution across the plate. Growth was scored visually as in the bulk fluid determinations, and cfu/ml calculated using the MPN method. Antibacterial activity on the surface was assessed by comparing cfu/cm$^2$ on untreated control coupons to those of treated coupons. The results are listed in Table 2.

TABLE 2

Antimicrobial activity of peptide coupons according to the invention

| Example No. | Untreated Coupon (cfu/cm2) | Peptide treated coupon (cfu/cm2) |
| --- | --- | --- |
| 1 | 8.8e3 | 1.7e3 |
| 2A | 4.3e4 | 2.75e2 |
| 2B | 4.3e4 | 1.1e2 |
| 2C | 4.3e4 | 2.2e2 |
| 2D Comparative | 3.4e4 | 6.9e4 |
| 2E Comparative | 3.4e4 | 3.1e5 |
| 3A | 4.2e4 | 2.0e3 |
| 3B | 4.2e4 | 7.5e3 |
| 3C | 4.2e4 | 2.0e4 |
| 4A | 2.65e5 | 1.7e2 |
| 4B | 2.65e5 | 1.7e1 |

TABLE 2-continued

Antimicrobial activity of peptide coupons according to the invention

| Example No. | Untreated Coupon (cfu/cm2) | Peptide treated coupon (cfu/cm2) |
| --- | --- | --- |
| 5 | 1.7e4 | 6.9e1 |
| 6 | 6.1e5 | 1.3e4 |
| 7 | 5.8e4 | 5.2e2 |

Example 9

This example illustrates the formation of an antimicrobial surface on a polyamide substrate and PG1 peptide to provide a antimicrobial surface.

Nylon 6,6 films (2×2 cm, 1 mil thick) were treated with a solution of paraformaldehyde (1.6 g) and chlorotrimethylsilane (15 mL) at 60° C. for 2 h; and washed as described in example 1 to provide chemically modified surfaces. The chemically modified films were immersed in 0.1M sodium carbonate (3 mL, pH 8.4); PG1 antimicrobial peptide (1 mg in 0.3 mL water) was added. The resulting cloudy mixture was heated to 80° C. and shaken for 1 h, and left at room temperature 15 overnight . The films were washed consecutively, with dd water (4 times), 0.1% wt TritonX-100 (2 times), and dd water (4 times); each wash with 15 mL portions and 15 min agitation. The films were finally washed for 1 hour with agitation in dd water, and dried in air.

Example 10

This example illustrates the efficacy of the antimicrobial surface using a mini-shake flask test.

A single colony of *Escherichia coli* ATCC 25922 was inoculated from a trypticase soy agar plate into TSB (15 mL) and incubated overnight at 37° C. The inoculum for the assay was prepared by diluting an aliquot of the incubated culture 1:10,000 into 10 mM phosphate buffer (pH 7.4), supplemented with M9 glucose to 5 wt %, to achieve a concentration of approximately $5 \times 10^5$ cfu/ml.

Treated films from example 9 were placed in a well in a 12 well microtitre plate. The above assay medium (2 mL) was added to the well. After covering the plate with a lid, the plate is placed into a 37° C. incubator on an orbital shaker and incubated for 6 h. Cfu/ml in the assay medium was determined at the beginning and end of each test. The bulk assay medium is sampled for viable cfu/ml by removing 4×20 microliter aliquots into 180 microliter of TSB in the first column of a 96 well microtitre plate and performing ten-fold serial dilutions. The plates were incubated overnight at 37° C., scored visually by observing the last well displaying visual growth, and the number of cfu/ml calculated using an Excel spreadsheet program to calculate the Most Probable Number (MPN) of viable cfu/ml in the original sample. Bacteria on the surface of the test sample were counted by rinsing the sample gently in phosphate buffer, then placing the sample in phosphate buffer (4 mL) and cavitating in a sonic bath for 5 min. The fluid was sampled for viable cfu/ml by performing a five-fold serial dilution and using the MPN method.

| Example No. | Untreated film (cfu/cm2) | peptide treated film (cfu/cm2) |
| --- | --- | --- |
| 9 | 5.1e4 | 1.1e1 |

What is claimed is:

1. A medical device having a durable antimicrobial polymeric surface, said surface comprising a chemically modified polymer substrate selected from the group consisting of polyamides, polyurethanes and polyureas and at least one linear cationic antimicrobial peptide having a net positive charge of greater than 1 at physiological pH, wherein said peptide is selected from the group consisting of:
PKGLKKLLKGLKKLLKL (SEQ ID NO: 1);
KGLKKLLKGLKKLLKL (SEQ ID NO: 2);
KGLKKLLKLLKKLLKL (SEQ ID NO: 3);
LKKLLKLLKKLLKL (SEQ ID NO: 4); and
LKKLLKLLKKLL (SEQ ID NO: 5);
and wherein said chemically modified surface is provided by a treating a polymer substrate with a first fluid comprising formaldehyde and a co-reactant selected from the group consisting of acid, anhydride, reactive halide, and mixtures thereof; wherein the formaldehyde and co-reactant are present in amounts effective to provide a polymer substrate with a chemically modified surface and wherein said peptide is bonded to the chemically modified polymer substrate.

2. The medical device of claim 1, wherein the polymer substrate is a film, nonwoven fabric or fiber.

3. The medical device of claim 1, wherein said device is selected from the group consisting of catheters, pacemaker leads, vascular grafts, blood tubing, balloons, shunts, cardiac-assist devices, and urological implants.

4. The medical device of claim 1, wherein the device is a barrier material selected from the group consisting of wound dressings, surgical gowns, gloves, aprons, and drapes.

5. A process for providing a durable antimicrobial surface on a polymer substrate comprising:
a) treating a polymer substrate with a first fluid comprising formaldehyde and a co-reactant selected from the group: acid, anhydride, reactive halide, or mixtures thereof wherein the formaldehyde and co-reactant are present in amounts effective to provide a polymer substrate with a chemically modified surface; and
b) treating the chemically modified surface of step (a) with an antimicrobial fluid comprising an effective amount of an antimicrobial peptide sufficient to provide a durable antimicrobial surface, wherein said peptide is selected from the group consisting of:
PKGLKKLLKGLKKLLKL (SEQ ID NO: 1);
KGLKKLLKGLKKLLKL (SEQ ID NO: 2);
KGLKKLLKLLKKLLKL (SEQ ID NO: 3);
LKKLLKLLKKLLKL (SEQ ID NO: 4); and
LKKLLKLLKKLL (SEQ ID NO: 5).

6. A process for providing a durable antimicrobial surface on a polymer substrate comprising:
a) (1) treating a polymer substrate with a first alternative fluid comprising formaldehyde and a hydroxymethylation catalyst wherein the formaldehyde and hydroxymethylation catalyst are present in an amount effective to provide a polymer substrate with a hydroxymethyl surface;
(2) treating the hydroxymethyl surface with a second alternative fluid comprising a reactant selected from the group: acid, anhydride, reactive halide, and mixtures thereof in an amount effective to provide a polymer substrate with a chemically modified surface; and
b) treating the chemically modified surface of step (a) (2), with an antimicrobial fluid comprising an effective amount of an antimicrobial peptide sufficient to provide a durable antimicrobial surface, wherein said peptide is selected from the group consisting of:
PKGLKKLLKGLKKLLKL (SEQ ID NO: 1);
KGLKKLLKGLKKLLKL (SEQ ID NO: 2);
KGLKKLLKLLKKLLKL (SEQ ID NO: 3);
LKKLLKLLKKLLKL (SEQ ID NO: 4); and
LKKLLKLLKKLL (SEQ ID NO: 5).

7. The process of claims 5 or 6, wherein the antimicrobial fluid further comprises an effective amount of base catalyst.

8. The process of claims 5 or 6 wherein the antimicrobial fluid further comprises a base catalyst selected from the group: potassium hydroxide, sodium hydroxide, potassium carbonate, sodium carbonate, trimethylamine, triethylamine, tripropylamine, diisopropylethylamine and tributyl amine.

9. The process of claims 5 or 6, wherein the polymer substrate of step (a) is comprised of one or more homopolymers, copolymers, block copolymers or graft polymers selected from the group: polyamide, polyurethane, and polyurea.

10. The process of claims 5 or 6, wherein the polymer substrate of step (a) is a thermoplastic polyurethane elastomer.

11. The process of claims 5 or 6, wherein said antimicrobial peptide is characterized by a weight average molecular weight of about 1000 to about 60,000 Daltons.

12. The process of claims 5 or 6, wherein said antimicrobial peptide is one or more linear cationic peptide(s).

13. The process of claims 5 or 6, wherein the durable antimicrobial surface is provided on a medical device.

14. The process of claims 5 or 6, wherein said formaldehyde is selected from the group: aqueous formaldehyde, paraformaldehyde and trioxane.

15. The process of claim 5 wherein the co-reactant of step (a) is selected from the group: trimethylsilylchloride, trimethylsilylbromide, and hydrogen chloride.

16. The process of claim 6 wherein the reactant of step (a) (2) is selected from the group: trimethylsilylchloride, trimethylsilylbromide, and hydrogen chloride.

17. The process of claim 5, wherein said first fluid consists essentially of paraformaldehyde and trimethylsilylchloride.

18. The process of claims 5 or 6, wherein treating the chemically modified surface with said antimicrobial fluid is performed at a reaction temperature of about 4° C. to about 100° C., for a reaction time of about 0.1 to about 10 hours.

19. The process of claim 6, wherein said hydroxymethylation catalyst is selected from the group: hydrogen chloride, sulfuric acid, glacial acetic acid formic acid, sodium hydroxide, potassium hydroxide, sodium carbonate and potassium carbonate.

20. The process of claims 5 or 6, wherein the polymer substrate is a nonwoven fabric.

21. The process of claims 5 or 6, wherein the polymer substrate is a fiber.

22. The process of claims 5 or 6, wherein the polymer substrate is a film.

23. The process of claim 5 or 6, wherein the polymer substrate is selected from the group: catheters, pacemaker leads, vascular grafts, blood tubing, balloons, shunts, cardiac-assist devices, and urological implants; and barrier materials selected from the group: wound dressings, surgical gowns, gloves, aprons, and drapes.

24. The process of claims 5 or 6, further comprising washing said durable antimicrobial surface with one or more wash solvents to remove excess antimicrobial peptide, base if used, and any byproducts; to provide a durable antimicrobial surface substantially free of non-bonded contaminants.

25. The process of claims 5 or 6, further comprising washing said durable antimicrobial surface with one or more wash solvents to remove excess antimicrobial peptide, base if used, and any byproducts; to provide a durable antimicrobial surface substantially free of non-bonded contaminants.

* * * * *

UNITED STATES PATENT AND TRADEMARK OFFICE
CERTIFICATE OF CORRECTION

PATENT NO.       : 7,601,361 B2                                         Page 1 of 1
APPLICATION NO.  : 11/242395
DATED            : October 13, 2009
INVENTOR(S)      : Lu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 702 days.

Signed and Sealed this

Fifth Day of October, 2010

David J. Kappos
*Director of the United States Patent and Trademark Office*